United States Patent [19]

Takase et al.

[11] Patent Number: 5,364,624
[45] Date of Patent: * Nov. 15, 1994

[54] WS7622A MONO- OR DI-SULFATE, PROCESS FOR PREPARATION THEREOF AND USE THEREOF

[75] Inventors: Shigehiro Takase, Ishioka; Hiroshi Hatanaka, Katasouma; Masami Ezaki, Tsukuba; Eisaku Tsujii, Tsukuba; Masanori Okamoto, Tsukuba; Nobuharu Shigematsu, Tsukuba; Masakuni Okuhara, Tsukuba, all of Japan

[73] Assignee: Fujisawa Pharmaceutical Co., Ltd., Osaka, Japan

[*] Notice: The portion of the term of this patent subsequent to Mar. 8, 2011 has been disclaimed.

[21] Appl. No.: 87,006

[22] Filed: Jul. 7, 1993

Related U.S. Application Data

[62] Division of Ser. No. 713,295, Jun. 11, 1991, Pat. No. 5,292,510.

[30] Foreign Application Priority Data

Jun. 29, 1990 [GB] United Kingdom .............. 9014546.7

[51] Int. Cl.$^5$ .............................................. A61K 35/74
[52] U.S. Cl. .................................... 424/117; 424/118
[58] Field of Search .............................. 424/117, 118

[56] References Cited

U.S. PATENT DOCUMENTS 5,021,240 6/1991 Hatawaka et al. .................. 424/118
5,167,958 12/1992 Hatawaka et al. .................. 424/118

Primary Examiner—Jerome D. Goldberg
Attorney, Agent, or Firm—Oblon, Spivak, McClelland, Maier & Neustadt

[57] ABSTRACT

A degenerative disease selected from the group consisting of cystic fibrosis, chronic bronchitis and bronchiectasia is treated by administering to a subject a therapeutically effective amount of WS7622A mono-or disulfate or pharmaceutically acceptable salt thereof.

1 Claim, 5 Drawing Sheets

WS7622A MONO- OR DI-SULFATE, PROCESS FOR PREPARATION THEREOF AND USE THEREOF

This is a division of application Ser. No. 07/713,295, filed on Jun. 11, 1991, now U.S. Pat. No. 5,292,510.

This invention relates to new WS7622A mono- or di-sulfate.

More particularly, this invention relates to new WS7622A mono- or di- sulfate and their pharmaceutically acceptable salts which have an human leukocyte elastase-inhibiting activity, to process for preparation thereof, and to a pharmaceutical composition comprising the same and to a method of use thereof.

This inventors of this invention prepared previously WS7622A substance which is used as a starting material in this invention, by culturing a strain of *Streptomyces resistomycificus* No. 7622 in a nutrient medium and filed a patent application covering the substance in various countries (cf. European Patent Application No. 90104500.5). *Streptomyces resistomycifiucs* No. 7622 was deposited with International Depositary Authority under the Budapest Treaty, the Fermentation Research Institute, Agency of Industrial Science and Technology (1–3, Higashi 1-chome, Tsukuba-shi, Ibaraki-ken, 305 Japan) under the accession number of FERM BP-2306 (the deposited date: Feb. 23, 1989).

The WS7622A substance, however, is insoluble in water and so the inventors of this invention studied on improvement of solubility of WS7622A substance in water so that they succeeded in improving solubility of WS7622A substance in water by sulfating WS7622A substance.

The WS7622A mono- or di- sulfate and their pharmaceutically acceptable salt of this invention can be prepared by sulfating WS7622A substance or its salt.

The starting material, WS7622A substance is the new compound and possesses the following physico-chemical properties.

Physico-chemical properties of WS7622A substance:
Appearance: colorless prism
Nature of substance: acidic
Color reaction: positive; cerium sulfate, iodine vapor negative; ninhydrin, Molish
Solubility: soluble; methanol, ethanol, n-butanol sparingly soluble; chloroform, acetone, ethyl acetate insoluble; water, n-hexane
Thin Layer Chromatography (TLC): chloroform-methanol (5:1, v/v) Rf 0.51 acetone-methanol (10:1) 0.62 (Kiesel gel 60 F254 silica gel plate, Merck)
Melting point: 250°–252° C. (dec.)
Specific rotation: $[\alpha]_D^{23} +36°$ (C=1.0, methanol)
UV spectrum: $\lambda_{max}^{MeOH}$ 287 nm ($\epsilon$=3600) $\lambda_{max}^{MeOH-HCl}$ 287 nm $\lambda_{max}^{MeOH-NaOH}$ 298 nm
Molecular formula: $C_{47}H_{63}N_9O_{13}$
Elemental analysis: calcd. ($C_{47}H_{63}N_9O_{13} \cdot 2H_2O$); C 56.56, H 6.77, N 12.63% found; C 56.65, H 6.62, N 12.27% Molecular weight: FAB-MS m/z 984 $(M+Na)^+$
Infrared absorption spectrum: $\lambda_{max}^{KBr}$ 3400, 3300, 3060, 2980, 2940, 1735, 1710, 1690, 1670, 1660, 1640, 1540, 1520, 1470, 1380, 1330, 1300, 1260, 1220, 1200, 1160, 1130, 1090, 1000, 980, 940, 920 cm$^{-1}$
$^1$H Nuclear magnetic resonance spectrum: (400 MHz, CD$_3$OD) δ

| | |
|---|---|
| 7.22–7.09 | (3H, m) |
| 6.88–6.77 | (3H, m) |
| 6.74 | (1H, s) |
| 6.46 | (1H, s) |
| 5.46 | (1H, m) |
| 5.18 | (1H, s) |
| 4.85 | (1H, s) |
| 4.77 | (1H, m) |
| 4.65 | (1H, m) |
| 4.50 | (1H, m) |
| 3.96 | (1H, m) |
| 3.91 | (1H, d, J=9Hz) |
| 3.60–3.47 | (2H, m) |
| 3.03 | (1H, m) |
| 2.90 | (3H, s) |
| 2.86 | (1H, m) |
| 2.59–2.49 | (2H, m) |
| 2.39 | (1H, m) |
| 2.29–2.16 | (2H, m) |
| 2.00 | (1H, m) |
| 1.84 | (1H, m) |
| 1.74 | (3H, d, J=6Hz) |
| 1.72–1.53 | (4H, m) |
| 1.44 | (3H, d, J=6Hz) |
| 1.12 | (1H, m) |
| 1.10 | (6H, d, J=6Hz) |
| 0.99 | (3H, d, J=6Hz) |
| 0.94 | (3H, d, J=6Hz) |

$^{13}$C Nuclear magnetic resonance spectrum: (100 MHz, CD$_3$OD) δ

| | |
|---|---|
| 179.7 | (s) |
| 176.3 | (s) |
| 174.7 | (s) |
| 173.3 | (s) |
| 172.4 | (s) |
| 171.4 | (s) |
| 170.3 | (s) |
| 165.8 | (s) |
| 160.2 | (s) |
| 145.7 | (s) |
| 145.6 | (s) |
| 137.5 | (s) |
| 134.0 | (d) |
| 131.4 | (s) |
| 130.6 | (d) × 2 |
| 129.8 | (s) |
| 129.1 | (d) × 2 |
| 129.1 | (s) |
| 127.6 | (d) |
| 119.1 | (d) |
| 118.0 | (d) |
| 76.0 | (d) |
| 73.4 | (d) |
| 63.1 | (d) |
| 61.4 | (d) |
| 57.1 | (d) |
| 53.6 | (d) |
| 52.7 | (d) |
| 50.5 | (d) |
| 39.9 | (t) |
| 36.1 | (t) |
| 35.8 | (d) |
| 31.8 | (q) |
| 31.0 | (t) |
| 30.8 | (d) |
| 29.9 | (t) |
| 29.7 | (t) |
| 25.2 | (t) |
| 22.3 | (t) |
| 20.2 | (q) |
| 20.0 | (q) × 2 |
| 19.7 | (q) |
| 19.5 | (q) |
| 13.3 | (q) |

Amino acid analysis:
WS7622A (1 mg) was hydrolyzed with 6N HCl (1 ml) at 110° C. for 20 hours and the mixture was evaporated to dryness. The obtained mixture was analyzed on Hitachi 835 automatic amino acid analyzer. Amino acid standard solution [Type H (Wako Chemicals 013-08391) and Type B (Wako Chemicals 016-08641) were used.] were used as reference.

As the result, threonine, valine, phenylalanine, ornithine, NH3 and unknown ninhydrin-positive components were detected.

The partial chemical structure of WS7622A is proposed as follows:

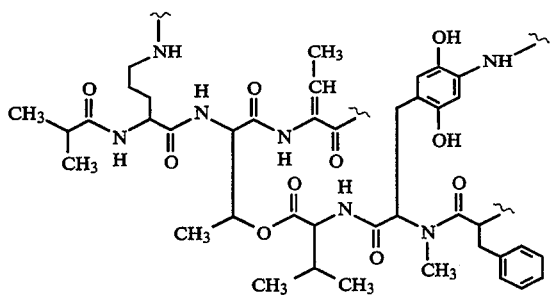

A salt of the WS7622A may include a salt with an inorganic or organic base such as an alkali metal salt (e.g. sodium salt, potassium salt, etc.), an alkaline earth metal salt (e.g. calcium salt, etc.), ammonium salt, ethanolamine salt, triethylamine salt, dicyclohexylamine salt or the like.

Suitable sulfating agents to be used for the preparation of the WS7622A mono- or di- sulfate and their pharmaceutically acceptable salt of this invention are chlorosulfonic acid, sulfamic acid, a combination of dicyclohexylcarbodiimide and sulfuric acid, a combination of dicyclohexylcarbodiimide and tetrabutylammonium hydrogen sulfate, sulfur trioxide adducts such as sulfur trioxide pyridine complex, sulfur trioxide trimethylamine complex, sulfur trioxide triethylamine complex, sulfur trioxide dioxane complex, sulfur trioxide dimethylaniline complex or the like.

The reaction is usually carried out in a conventional solvent, such as methylene chloride, chloroform, benzene, toluene, pyridine, diethyl ether, dioxane, tetrahydrofuran, acetone, acetonitrile, ethyl acetate, N,N-dimethylformamide or any other organic solvent which does not adversely affect the reaction.

The reaction temperature is not critical and the reaction can be carried out under cooling, at ambient temperature, or under heating.

This reaction may be preferably conducted in the presence of a base. Suitable base may be an inorganic base such as alkali or alkaline earth metal hydroxide (e.g. sodium hydroxide, potassium hydroxide, calcium hydroxide, etc.), alkali metal bicarbonate (e.g. sodium bicarbonate, potassium bicarbonate, etc.), alkali or alkaline earth metal carbonate (e.g. sodium carbonate, potassium carbonate, calcium carbonate, etc.), alkali metal phosphate (e.g. sodium dihydrogenphosphate, potassium dihydrogenphosphate, disodium hydrogenphosphate, dipotassium hydrogenphosphate, etc.) or an organic base such as alkali metal alkoxide (e.g. sodium methoxide, potassium ethoxide, etc.), amine (e.g. triethylamine, pyridine, lutidine, etc.).

The WS7622A mono- or di- sulfate and their pharmaceutically acceptable salt are the new compound, and among them, the di-sodium salt of WS7622A di-sulfate and the di-potassium salt of WS7622A di-sulfate have the following physico-chemical properties, respectively.

BRIEF DESCRIPTION OF THE DRAWINGS

Di-sodium salt of WS7622A di-sulfate
FIG. 1—Infrared Absorption Spectrum
FIG. 2—$^1$H Nuclear Magnetic Resonance Spectrum
FIG. 3—$^{13}$C Nuclear Magnetic Resonance Spectrum
Di-potassium salt of WS7622A di-sulfate
FIG. 4—Infrared Absorption Spectrum
FIG. 5—$^1$H Nuclear Magnetic Resonance Spectrum Di-potassium salt of WS7622A di-sulfate:
Appearance: colorless crystals
Solubility: soluble; water, methanol insoluble; chloroform, n-hexane
Melting point: 257°–263° C. (dec.)
Specific rotation: $[\alpha]_D^{23} + 37.5°$ (C=1.0, methanol)
Molecular formula: $C_{47}H_{61}N_9O_{19}S_2Na_2$
Elemental analysis: calcd. ($C_{47}H_{61}N_9O_{19}S_2Na_2 \cdot 6H_2O$); C 44.30, H 5.77, N 9.89, S 5.03, Na 3.61% found: C 44.98, H 5.90, N 10.06, S 5.00, Na 3.98%
Molecular weight: FAB-MS m/z 1188 (M+Na)$^+$
Thin layer chromatography:

| Stationary phase | Developing solvent | Rf value |
| --- | --- | --- |
| silica gel (Merck Art 5715) | CHCl$_3$—CH$_3$OH—H$_2$O (65:25:4) | 0.11 |
| | n-butanol-acetic acid-water (4:2:1) | 0.29 |

Figure 1:
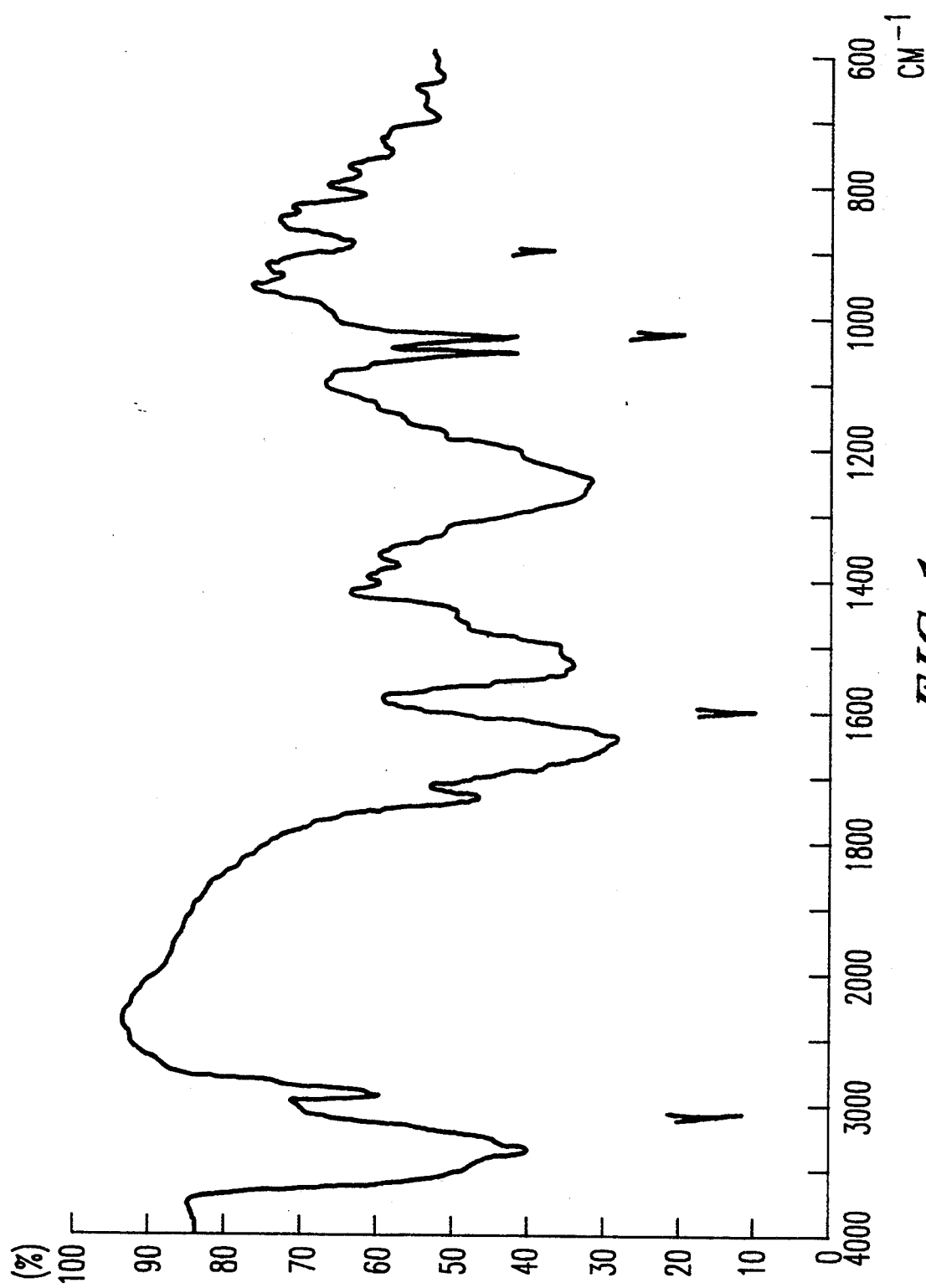
Figure 2:
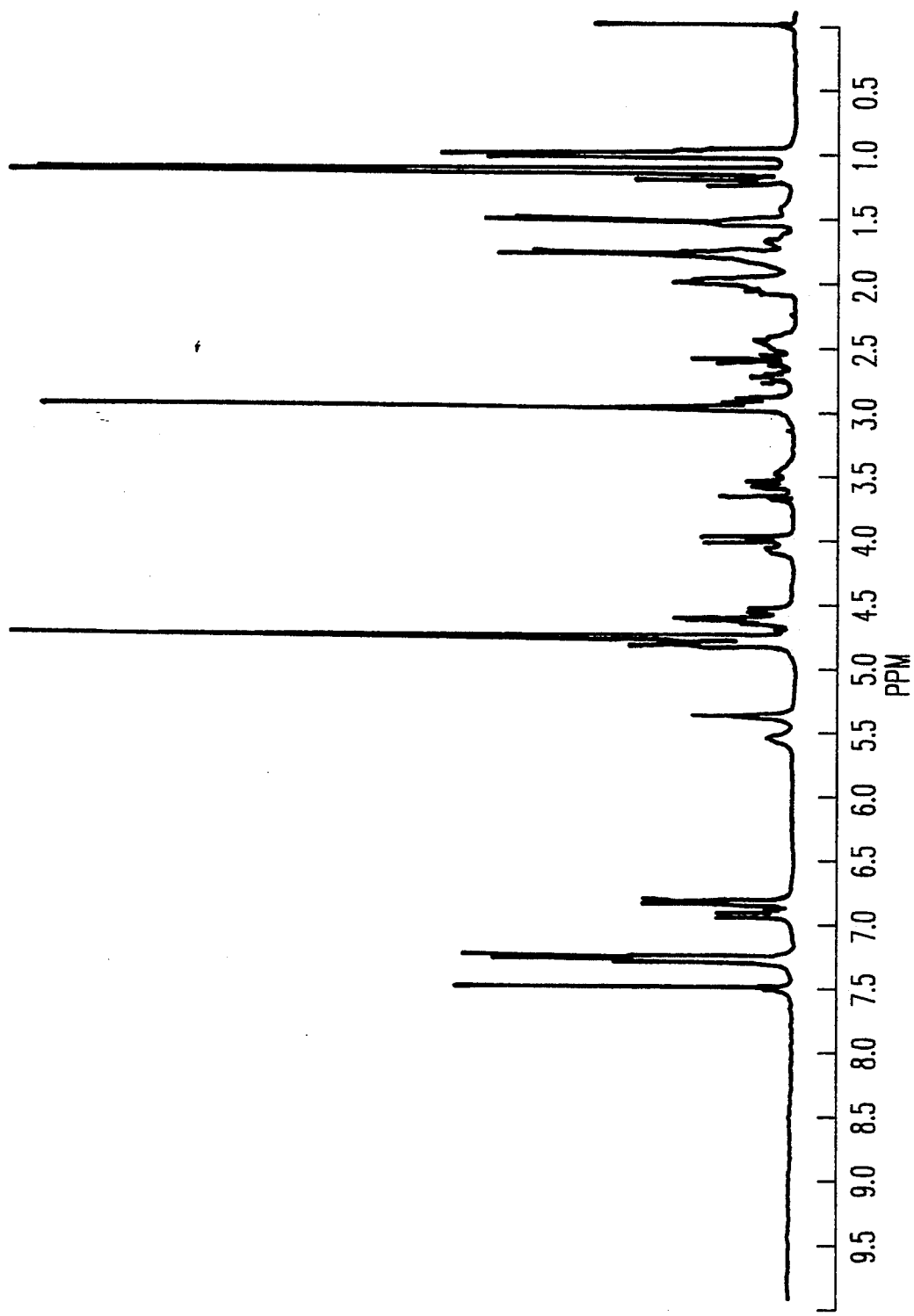

Infrared absorption spectrum (attached FIG. 1 ): $\nu_{max}^{KBr}$ 3360, 2960, 1735, 1660, 1640, 1530, 1500, 1380, 1250, 1200, 1060, 1030, 940, 890 cm$^{-1}$ $^1$H Nuclear magnetic resonance spectrum (attached FIG. 2): (400 MHz, D$_2$O) δ

| | |
| --- | --- |
| 7.50 | (1H, s) |
| 7.27 | (1H, s) |
| 7.33–7.24 | (3H, m) |
| 6.94 | (1H, q, J=7Hz) |
| 6.85 | (2H, br d, J=8Hz) |
| 5.53 | (1H, m) |
| 5.37 | (1H, m) |
| 4.80 | (1H, br s) |
| 4.63–4.57 | (2H, m) |
| 4.53 | (1H, m) |
| 4.06 | (1H, m) |
| 3.99 | (1H, d, J=10Hz) |
| 3.56 | (1H, br d, J=14Hz) |
| 3.46 | (1H, m) |
| 2.97 | (3H, s) |
| 2.97–2.88 | (2H, m) |
| 2.72 | (1H, m) |
| 2.59 | (1H, m) |
| 2.51–2.38 | (2H, m) |
| 2.09–1.91 | (4H, m) |
| 1.82–1.60 | (3H, m) |
| 1.77 | (3H, d, J=7Hz) |
| 1.50 | (3H, d, J=6.5Hz) |
| 1.40 | (1H, m) |
| 1.11 | (6H, d, J=7Hz) |
| 0.99 | (3H, d, J=6.5Hz) |
| 0.97 | (3H, d, J=6.5Hz) |

Figure 3:
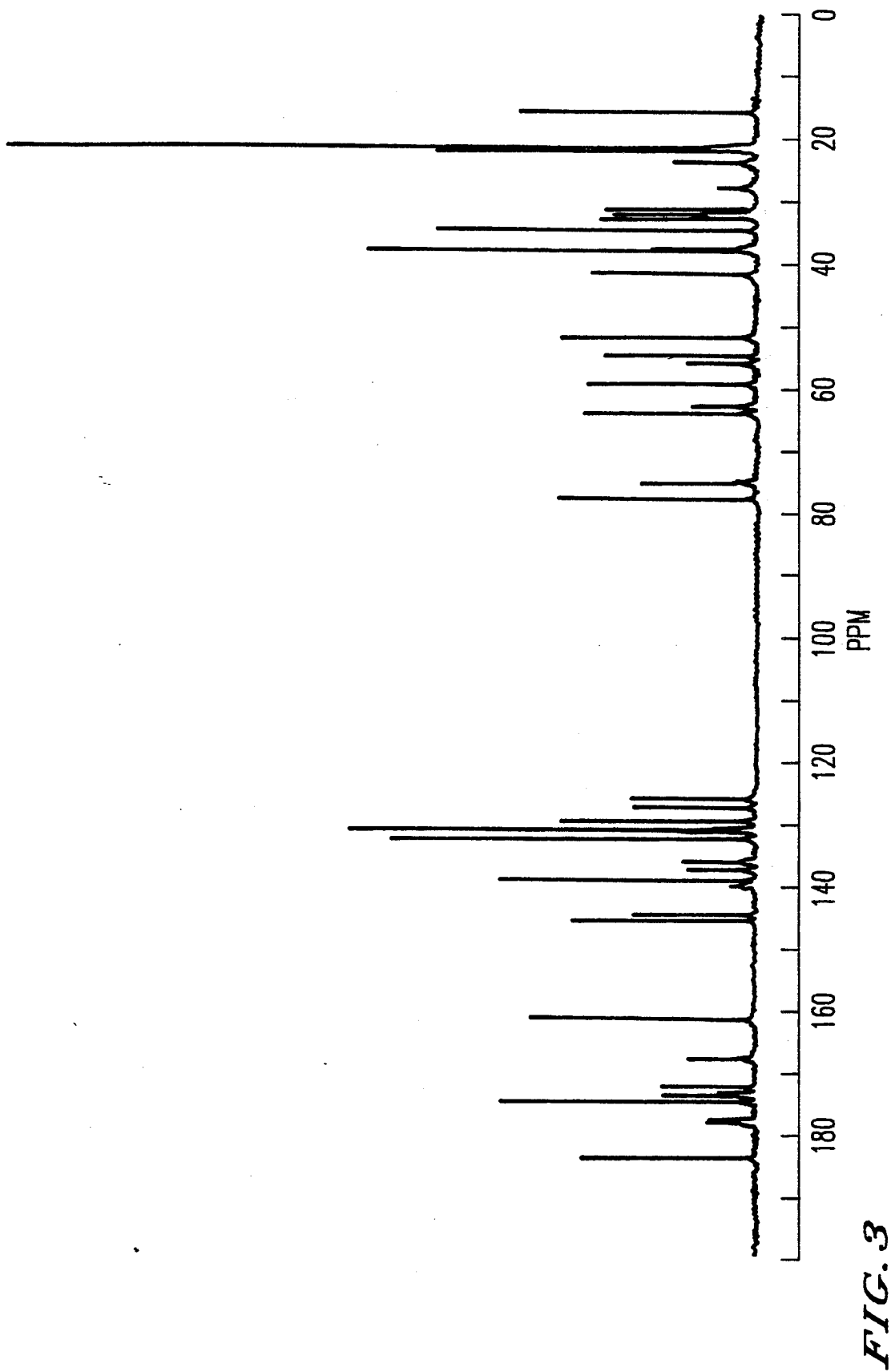

$^{13}$C Nuclear magnetic resonance spectrum ( attached FIG. 3): (100 MHz, D$_2$O) δ

| | |
| --- | --- |
| 183.6 | (s) |
| 177.9 | (s) |
| 177.7 | (s) |
| 174.8 | (s) |
| 173.8 | (s) |

-continued

| | |
|---|---|
| 173.3 | (s) |
| 172.4 | (s) |
| 167.8 | (s) |
| 161.5 | (s) |
| 145.5 | (s) |
| 144.9 | (s) |
| 139.6 | (d) |
| 139.0 | (s) |
| 137.0 | (s) |
| 136.0 | (s) |
| 132.3 | (d) × 2 |
| 131.0 | (d) × 2 |
| 129.6 | (d) |
| 127.4 | (d) |
| 125.9 | (d) |
| 77.4 | (d) |
| 75.1 | (d) |
| 63.8 | (d) |
| 62.7 | (d) |
| 59.1 | (d) |
| 55.9 | (d) |
| 54.9 | (d) |
| 51.9 | (d) |
| 41.9 | (t) |
| 37.2 | (d) |
| 36.9 | (t) |
| 34.1 | (q) |
| 32.3 | (d) |
| 31.9 | (t) |
| 31.8 | (t) |
| 31.2 | (t) |
| 27.5 | (t) |
| 23.7 | (t) |
| 21.7 | (q) |
| 21.4 | (q) × 2 |
| 21.3 | (q) |
| 21.1 | (q) |
| 15.5 | (q) |

Amino acid analysis:

Di-sodium salt of WS7622A di-sulfate (1 mg) was hydrolyzed with 6N HCl (1 ml) at 110° C. for 20 hours and the mixture was evaporated to dryness. The obtained mixture was analyzed on Hitachi 835 automatic amino acid analyzer. Amino acid standard solution [Type H (Wako Chemicals 013-08391) and Type B (Wako Chemicals 016-08641) were used.] were used as reference.

As the result, threonine, valine, phenylalanine, ornithine, NH₃ and unknown ninhydrin-positive components were detected.

The partial chemical structure of di-sodium salt of WS7622A di-sulfate is proposed as follows:

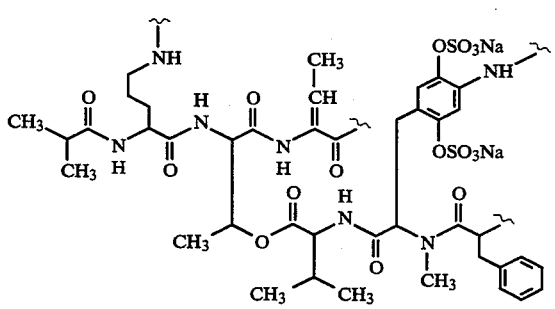

Di-potassium salt of WS7622A di-sulfate:
Appearance: colorless amorphous powder
Solubility: soluble; water, methanol insoluble; chloroform, n-hexane
Melting point:230°–237° C. (dec.)
Specific rotation: $[\alpha]_D^{23} + 34°$ (C=1.0, methanol)

Molecular formula: $C_{47}H_{61}N_9O_{19}S_2K_2$
Elemental analysis: calcd. $(C_{47}H_{61}N_9O_{19}S_2K_2 \cdot 6H_2O)$;
C 43.21, H 5.63, N 9.65, S 4.91, K 5.99% found: C 43.96, H 5.44, N 9.97, S 5.09, K 4.49%
Molecular weight: FAB-MS m/z 1236 (M+K)+
Thin layer chromatography:

| Stationary phase | Developing solvent | Rf value |
|---|---|---|
| silica gel (Merck Art 5715) | CHCl₃—CH₃OH—H₂O (65:25:4) | 0.13 |

Figure 4:
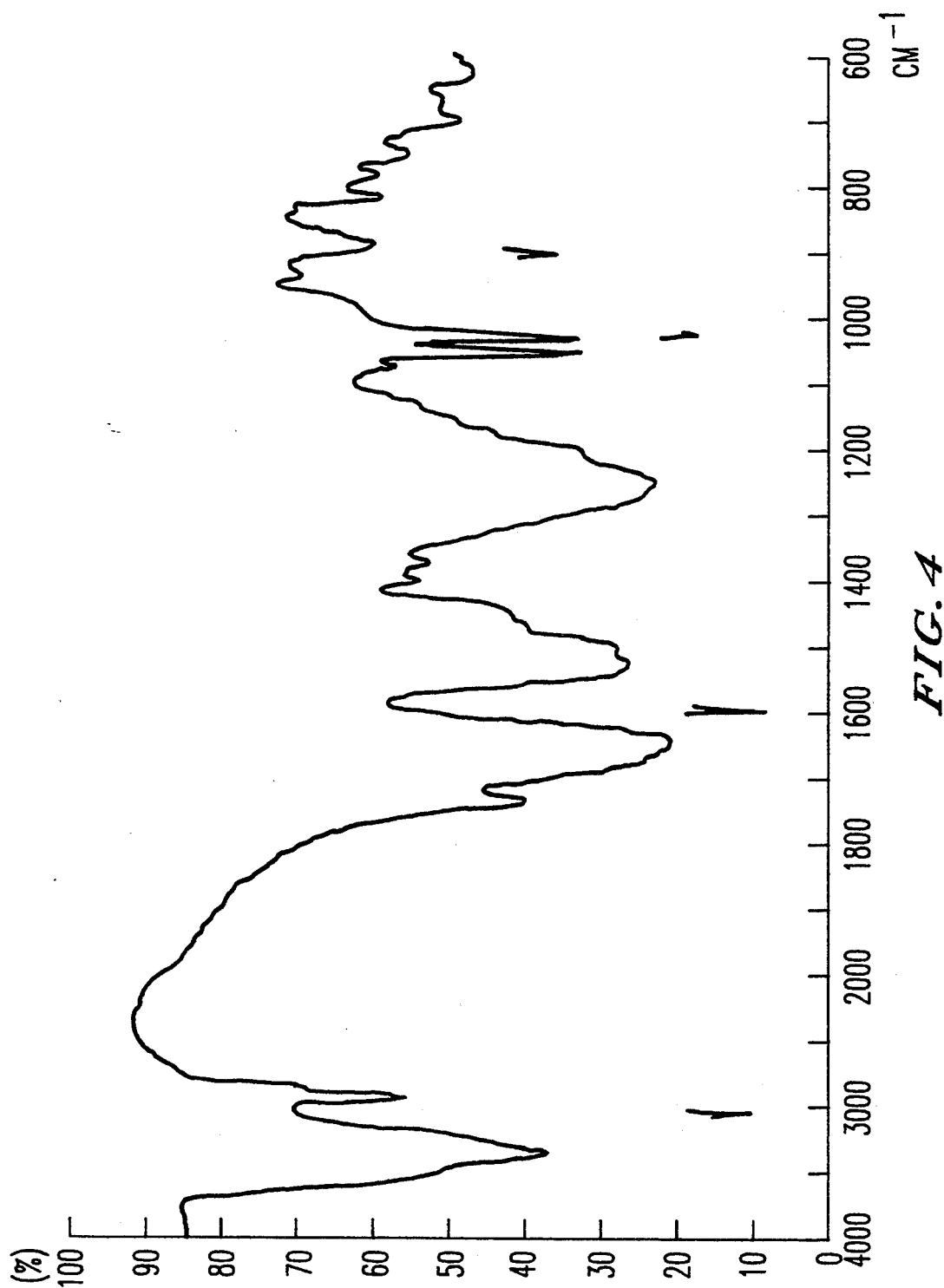

Infrared absorption spectrum (attached FIG. 4): $v_{max}^{KBr}$ 3360, 2960, 1735, 1660, 1640, 1530, 1500, 1405, 1380, 1250, 1200, 1050, 1030, 940, 890 cm⁻¹

Figure 5:
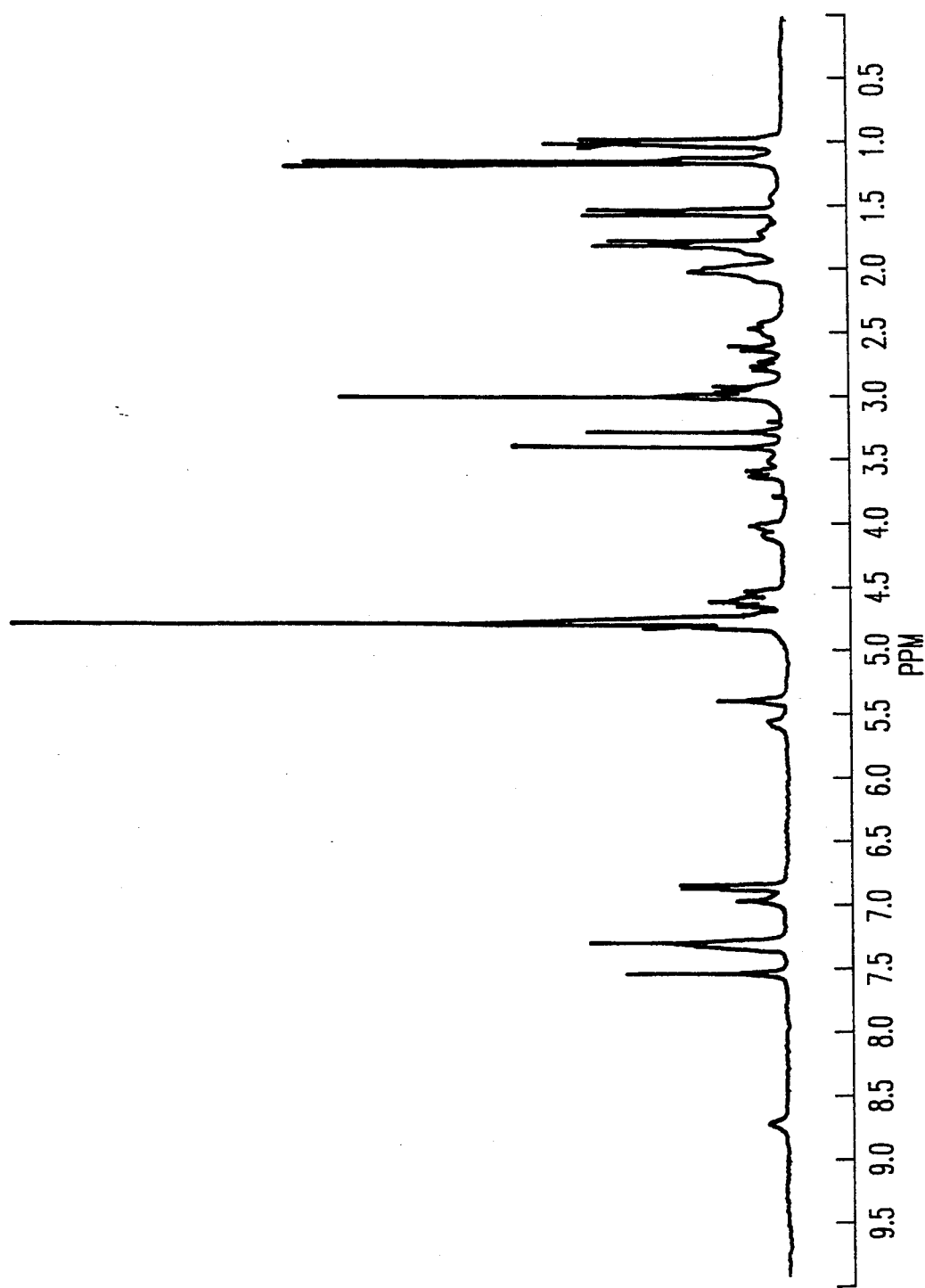

¹H Nuclear magnetic resonance spectrum (attached FIG. 5): (400 MHz, D₂O) δ

| | |
|---|---|
| 7.52 | (1H, s) |
| 7.28 | (1H, s) |
| 7.34–7.25 | (3H, m) |
| 6.96 | (1H, q, J=7Hz) |
| 6.87 | (2H, br d, J=8Hz) |
| 5.56 | (1H, m) |
| 5.40 | (1H, m) |
| 4.84 | (1H, br s) |
| 4.70–4.55 | (3H, m) |
| 4.10 | (1H, m) |
| 4.03 | (1H, m) |
| 3.60 | (1H, br d, J=14Hz) |
| 3.50 | (1H, m) |
| 3.00 | (3H, s) |
| 3.00–2.85 | (2H, m) |
| 2.76 | (1H, m) |
| 2.62 | (1H, m) |
| 2.55–2.40 | (2H, m) |
| 2.12–1.95 | (4H, m) |
| 1.90–1.65 | (3H, m) |
| 1.79 | (3H, d, J=7Hz) |
| 1.53 | (3H, d, J=6.5Hz) |
| 1.45 | (1H, m) |
| 1.14 | (6H, d, J=7Hz) |
| 1.02 | (3H, d, J=6.5Hz) |
| 1.00 | (3H, d, J=6.5Hz) |

Amino acid analysis:

Di-potassium salt of WS7622A di-sulfate (1 mg) was hydrolyzed with 6N HCl (1 ml) at 110° C. for 20 hours and the mixture was evaporated to dryness. The obtained mixture was analyzed on Hitachi 835 automatic amino acid analyzer. Amino acid standard solution [Type H (Wako Chemicals 013-08391) and Type B (Wako Chemicals 016-08641) were used.] were used as reference.

As the result, threonine, valine, phenylalanine, ornithine, NH₃ and unknown ninhydrin-positive components were detected.

The partial chemical structure of di-potssium salt of WS7622A di-sulfate is proposed as follows:

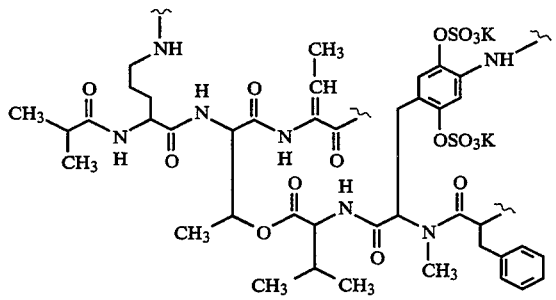

A pharmaceutically acceptable salt of the WS7622A mono- or di- sulfate may include mono- or di- salt with an inorganic or organic base such as an alkali metal salt (e.g. sodium salt, potassium salt, etc.), an alkaline earth metal salt (e.g. calcium salt, etc.), ammonium salt, ethanolamine salt, triethylamine salt, dicyclohexylamine salt, pyridine salt or the like.

The WS7622A mono- or di- sulfate and their pharmaceutically acceptable salt have a human leukocyte elastase-inhibiting activity and is useful as human leukocyte elastase inhibitors for treating degenerative diseases, for example, pulmonary emphysema, atherosclerosis, rheumatiod arthritis, osteoarthritis, psoriasis, pancreatitis, adult respiratory distress syndrome, cystic fibrosis, chronic bronchitis, bronchiectasia and the like, and further is useful for treatment of asthma, graft rejection, nephritis and sepsis.

In order to illustrate the usefulness of the WS7622A mono- or di- sulfate and their pharmaceutically acceptable salt, pharmacological test data thereof are shown below.

1. Protease Inhibition assay
(1) Method:

A buffer used throughout the assay was 0.1M HEPES (N-(2-hydroxyethyl)piperazine-N'-2-ethanesulfonic acid) containing 0.5M NaCl, pH 7.5. Twenty-five microliters of 2 mM methoxysuccinyl-(Ala)$_2$-Pro-Val-p-nitroanilide (100 mM of dimethyl sulfoxide solution were diluted in the buffer) and 50 $\mu$l of sample (10 $\mu$l of sample in organic solvent was diluted 5-fold in the buffer) were mixed in wells of 96 well-microliter plate. An absorbance of the mixture in wavelength at 415 nm was measured by a microplate reader (Corona Electric Co., Ibaraki, Japan). After the measurement, 25 $\mu$l of 6 $\mu$g/ml human sputum elastase (HSE) and stand for 30 min at room temperature. Then, the absorbance at 415 nm was measured. Percent inhibition by drug was determined by 100×(1-"r" inhibitor present/"r" inhibitor absent), where "r" is absorbance alter 30 min incubation minus absorbance before enzyme addition. Effects of inhibitors against other proteases were assayed similarly using N-succinyl-(Ala)$_3$-p-nitroanilide for porcine pancrease elastase (Type IV, 5 $\mu$g/ml final), N-alpha-benzoyl-Arg-p-nitroanilide for bovine pancreas trypsin (Type I, 16 $\mu$g/ml final), methoxysuccinyl-(Ala)$_2$-Pro-Met-p-nitroanilide for bovine pancreas chymotrypsin (Type II, 1.5 $\mu$g/ml final). HSE were obtained from Elastin Products Company Inc., MO, U.S.A. All other substrates and proteases were purchased from Sigma Chemicals Co.

(2) Result:

Inhibitory effect of di-sodium salt of WS7622A di-sulfate and di-potassium salt of WS7622A di-sulfate on several serine protease activity

| substance (M) | $IC_{50}$ (M) | | | |
|---|---|---|---|---|
| | Human sputum elastase | Porcine pancreas elastase | Trypsin (bovine) | Chymotrypsin (bovine) |
| di-sodium salt of WS7622A di-sulfate | $3.5 \times 10^{-8}$ | $4.9 \times 10^{-8}$ | $1.8 \times 10^{-4}$ | $2.0 \times 10^{-7}$ |
| di-potassium salt of WS7622A di-sulfate | $5.9 \times 10^{-8}$ | $4.9 \times 10^{-8}$ | $2.9 \times 10^{-4}$ | $2.0 \times 10^{-7}$ |

Each value was expressed as 50% inhibitory concentration ($IC_{50}$).

2. Determination of the activity in elastase-induced pulmonary damage.
(1) Method:

Hamsters under pentobarbital anesthesia were used. Saline or saline-containing human sputum elastase was instilled intratracheally via a small incision in the ventral neck region using 1-ml syringe with a 27-gauge needle. After 3 hours, animals were sacrificed by $CO_2$ asphyxiation, each animal's trachea was reexposed. The lungs were then laveged using a 2.5-ml aliquot of saline and then withdrawing the saline, yielding a final volume of approximately 1.5 ml bronchoalveolar lavage (BAL) fluid from each animal.

The cells of BAL fluid were collected by centrifugation and were then diluted with distilled water to disrupt, and the hemoglobin contents determined spectrophotometrically at 541 nm.

Test drugs were dissolved in salin and instilled intratracheally in the same manner as used to instill elastase, at 5 minutes before instillation of elastase.

(2) Result:

| Inhibitory effect on elastase-induced lung hemorrhage | | | |
|---|---|---|---|
| Test compound | 5 min predose ($\mu$g/site) | Hemorrhage (OD 541 nm) | % inhibition |
| Normal | — | 0.31 ± 0.12 | — |
| control | — | 29.35 ± 2.9 | — |
| di-sodium salt of WS7622A di-sulfate | 1 | 19.06 ± 1.40* | 35.4 |
| | 10 | 9.75 ± 4.82* | 67.5 |
| | 100 | 0.28 ± 0.05*** | 100.1 |
| di-potassium salt of WS7622A di-sulfate | 1 | 19.71 ± 1.20* | 33.2 |
| | 10 | 10.73 ± 1.20** | 64.1 |
| | 100 | 0.35 ± 0.16*** | 99.9 |

*$p < 0.05$, $p < 0.01$, *$p < 0.001$ compared with control group (Student t test)

Pharmaceutical compositions of this invention can be used in a conventional pharmaceuticalformssuch as injections, inhalations, powders, fine granules, granules, tablets, dragee, microcapsules, capsules, suppository, solution, suspension, emulsion syrups and the like. If desired, diluents or disintegrators (e.g. sucrose, lactose, starch, crystalline cellulose, low-substituted hydroxypropyl cellulose, synthetic aluminum silicate, etc.), binding agents (e.g. cellulose, methylcellulose, hydroxypropylcellulose, hydroxypropylmethylcellulose, poiypropylpyrrolidone, polyvinylpyrrolidone, gelatin, gum arabic, polyethyleneglycol, etc.), coloring agents, sweeting agents, lubricant (e.g. magnesium stearate, etc.) or the like, may be dispensed with said composition.

The dosage of said composition of this invention depends on the patient's age, body weight, condition, etc., and it is generally administered by the oral route at the daily dose level of 100 mg to 10 g as the object compound or its pharmaceutically acceptable salt, preferably 1 g to 5 g on the same basis, at the interval of 1 to 3 times a day. Typical unit doses may be 50 mg, 100 mg, 200 mg, 500 mg, 1 g and the like, although these are only examples and not limitative, of course.

The following Examples are given for the purpose of illustrating this invention.

EXAMPLE 1

In a 300 ml three-necked flask were placed sulfur trioxide trimethylamine complex (13.9 g, Aldrich), anhydrous potassium carbonate (6.9 g) and WS7622A substance (10 g), and anhydrous dimethylformamide (50 ml) was added thereto and the mixture was vigorously stirred at room temperature overnight.

The mixture was evaporated to dryness under reduced pressure and the residue was dissolved in ice-water (300 ml) and charged on a column of HP20ss (9.6×25 cm). The column was washed with water (10 l) and eluted with MeOH-H$_2$O (4:6) (2 l). The product fractions were collected and evaporated to dryness to give a powder. The powder was dissolved in H$_2$O (70 ml) and passed through a column of AG50W-X4 (Na$^+$ form, 4×32 cm, Bio-Rad laboratories) and evaporated to dryness. The obtained powder (11.2 g) was recrystallized from hot ethanol (50 ml) to give 10.6 g of di-sodium salt of WS7622A di-sulfate as colorless crystals.

EXAMPLE 2

In a 300 ml three-necked flask were placed sulfur trioxide trimethylamine complex (13.9 g, Aldrich), anhydrous potassium carbonate (6.9 g) and WS7622A substance (10 g), and anhydrous dimethylformamide (50 ml) was added thereto and the mixture was vigorously stirred at room temperature overnight.

The mixture was evaporated to dryness under reduced pressure and the residue was dissolved in ice-water (300 ml) and charged or a column of HP20ss (9.6×25 cm). The column was washed with water (10 l) and eluted with MeOH-H$_2$O (4:6) (2 l). The product fractions were collected and evaporated to dryness to give 11.8 g of di-potassium salt of WS7622A di-sulfate as a colorless powder.

We claim:

1. A method of treating a degenerative disease selected from the group consisting of cystic fibrosis, chronic bronchitis and bronchiectasia in a subject comprising:
administering to said subject a therapeutically effective amount of WS7622A mono or di-sulfate or pharmaceutically acceptable salt thereof, wherein the disodium salt of WS7622A disulfate and the dipotassium salt of WS7622A disulfate have the following physicochemical properties:

Di-sodium salt of WS7622A di-sulfate:
Appearance: colorless crystals
Solubility: soluble; water, methanol insoluble; chloroform, n-hexane
Melting point: 257°–263° C. (dec.)
Specific rotation: $[\alpha]_D^{23}$ +37.5° (C=1.0, methanol)
Molecular formula: $C_{47}H_{61}N_9O_{19}S_2Na_2$
Elemental analysis: calcd. ($C_{47}H_{61}N_9O_{19}S_2Na_2 \cdot 6H_2O$); C 44.30, H 5.77, N 9.89, S 5.03, Na 3.61% found: C 44.98, H 5.90, N 10.06, S 5.00, Na 3.98%
Molecular weight: FAB-MS m/z 1188 (M+Na)$^+$
Thin layer chromatography:

| Stationary phase | Developing solvent | Rf value |
| --- | --- | --- |
| silica gel (Merck Art 5715) | CHCl$_3$—CH$_3$OH—H$_2$O (65:25:4) | 0.11 |
| | n-butanol-acetic acid-water (4:2:1) | 0.29 |

Infrared absorption spectrum (attached FIG. 1): $\nu_{max}^{KBr}$ 3360, 2960 1735, 1660, 1640, 1530, 1500, 1380, 1250, 1200, 1060, 1030, 940, 890 cm$^{-1}$ $^1$H Nuclear magnetic resonance spectrum (attached FIG. 2 ): (400 MHz, D$_2$O) δ

| | |
| --- | --- |
| 7.50 | (1H, s) |
| 7.27 | (1H, s) |
| 7.33–7.24 | (3H, m) |
| 6.94 | (1H, q, J=7Hz) |
| 6.85 | (2H, br d, J=8Hz) |
| 5.53 | (1H, m) |
| 5.37 | (1H, m) |
| 4.80 | (1H, br s) |
| 4.63–4.57 | (2H, m) |
| 4.53 | (1H, m) |
| 4.06 | (1H, m) |
| 3.99 | (1H, d, J=10Hz) |
| 3.56 | (1H, br d, J=14Hz) |
| 3.46 | (1H, m) |
| 2.97 | (3H, s) |
| 2.97–2.88 | (2H, m) |
| 2.72 | (1H, m) |
| 2.59 | (1H, m) |
| 2.51–2.38 | (2H, m) |
| 2.09–1.91 | (4H, m) |
| 1.82–1.60 | (3H, m) |
| 1.77 | (3H, d, J=7Hz) |
| 1.50 | (3H, d, J=6.5Hz) |
| 1.40 | (1H, m) |
| 1.11 | (6H, d, J=7Hz) |
| 0.99 | (3H, d, J=6.5Hz) |
| 0.97 | (3H, d, J=6.5Hz) |

$^{13}$C Nuclear magnetic resonance spectrum (attached FIG. 3): (100 MHz, D$_2$O) δ

| | |
| --- | --- |
| 183.6 | (s) |
| 177.9 | (s) |
| 177.7 | (s) |
| 174.8 | (s) |
| 173.8 | (s) |
| 173.3 | (s) |
| 172.4 | (s) |
| 167.8 | (s) |
| 161.5 | (s) |
| 145.5 | (s) |
| 144.9 | (s) |
| 139.6 | (d) |
| 139.0 | (s) |
| 137.0 | (s) |
| 136.0 | (s) |
| 132.3 | (d) × 2 |
| 131.0 | (d) × 2 |
| 129.6 | (d) |
| 127.4 | (d) |
| 125.9 | (d) |
| 77.4 | (d) |
| 75.1 | (d) |
| 63.8 | (d) |
| 62.7 | (d) |
| 59.1 | (d) |
| 55.9 | (d) |
| 54.9 | (d) |
| 51.9 | (d) |
| 41.9 | (t) |
| 37.2 | (d) |
| 36.9 | (t) |
| 34.1 | (q) |
| 32.3 | (d) |

-continued

| | |
|---|---|
| 31.9 | (t) |
| 31.8 | (t) |
| 31.2 | (t) |
| 27.5 | (t) |
| 23.7 | (t) |
| 21.7 | (q) |
| 21.4 | (q) × 2 |
| 21.3 | (q) |
| 21.1 | (q) |
| 15.5 | (q) |

Amino acid analysis:
  Di-sodium salt of WS7622A di-sulfate (1 mg) was hydrolyzed with 6N HCl (1 ml) at 110° C. for 20 hours and the mixture was evaporated to dryness;
  The obtained mixture was analyzed on Hitachi 835 automatic amino acid analyzer.
  Amino acid standard solution [Type H (Wako Chemicals 013-08391) and Type B (Wako Chemicals 016-08641) were used.] were used as reference;
  As the result, threonine, valine, phenylalanine, ornithine, $NH_3$ and unknown ninhydrin-positive components were detected;

Di-potassium salt of WS7622A di-sulfate:
Appearance: colorless amorphous powder
Solubility: soluble; water, methanol insoluble; chloroform, n-hexane
Melting point: 230°–237° C. (dec.)
Specific rotation: $[\alpha]_D^{23} + 34°$ (C=1.0, methanol)
Molecular formula: $C_{47}H_{61}N_9O_{19}S_2K_2$
Elemental analysis: calcd. ($C_{47}H_{61}N_9O_{19}S_2K_2 \cdot 6H_2O$); C 43.21, H 5.63, N 9.65, S 4.91, K 5.99% found: C 43.96, H 5.44, N 9.97, S 5.09, K 4.49%
Molecular weight: FAB-MS m/z 1236 $(M+K)^+$
Thin layer chromatography:

| Stationary phase | Developing solvent | Rf value |
|---|---|---|
| silica gel (Merck Art 5715) | $CHCl_3$—$CH_3OH$—$H_2O$ (65:25:4) | 0.13 |

Infrared absorption spectrum (attached FIG. 4): $\nu_{max}^{KBr}$ 3360, 2960, 1735, 1660, 1640, 1530, 1500, 1405, 1380, 1250, 1200, 1050, 1030, 940, 890 cm$^{-1}$ $^1$H Nuclear magnetic resonance spectrum (attached FIG. 5): (400 MHz, $C_2O$) δ

| | |
|---|---|
| 7.52 | (1H, s) |
| 7.28 | (1H, s) |
| 7.34–7.25 | (3H, m) |
| 6.96 | (1H, q, J=7Hz) |
| 6.87 | (2H, br d, J=8Hz) |
| 5.56 | (1H, m) |
| 5.40 | (1H, m) |
| 4.84 | (1H, br s) |
| 4.70–4.55 | (3H, m) |
| 4.10 | (1H, m) |
| 4.03 | (1H, m) |
| 3.60 | (1H, br d, J=14Hz) |
| 3.50 | (1H, m) |
| 3.00 | (3H, s) |
| 3.00–2.85 | (2H, m) |
| 2.76 | (1H, m) |
| 2.62 | (1H, m) |
| 2.55–2.40 | (2H, m) |
| 2.12–1.95 | (4H, m) |
| 1.90–1.65 | (3H, m) |
| 1.79 | (3H, d, J=7Hz) |
| 1.53 | (3H, d, J=6.5Hz) |
| 1.45 | (1H, m) |
| 1.14 | (6H, d, J=7Hz) |
| 1.02 | (3H, d, J=6.5Hz) |
| 1.00 | (3H, d, J=6.5Hz) |

Amino acid analysis:
  Di-potassium salt of WS7622A di-sulfate (1 mg) was hydrolyzed with 6N HCl (1 ml) at 110° C. for 20 hours and the mixture was evaporated to dryness;
  The obtained mixture was analyzed on Hitachi 835 automatic amino acid analyzer;
  Amino acid standard solution [Type H (Wako Chemicals 013-08391) and Type B (Wako Chemicals 016-08641) were used] were used as reference. As the result, threonine, vaiine, phenylalanine, ornithine, $NH_3$ and unknown ninhydrin-positive components were detected.

* * * * *